United States Patent [19]

Ingall et al.

[11] Patent Number: 5,955,447

[45] Date of Patent: *Sep. 21, 1999

[54] N-ALKYL-2-SUBSTITUTED ATP ANALOGUES FOR TREATMENT OF EMBOLIC DISEASE CONDITIONS

[75] Inventors: Anthony H Ingall, Loughborough; Peter A Cage, Shepshed; Nicholas D Kindon, Ibstock, all of United Kingdom

[73] Assignee: Astra Pharmaceuticals Limited, London, United Kingdom

[*] Notice: This patent is subject to a terminal disclaimer.

[21] Appl. No.: 08/918,670

[22] Filed: Aug. 28, 1997

Related U.S. Application Data

[62] Division of application No. 08/512,979, Aug. 9, 1995, Pat. No. 5,721,219, which is a continuation of application No. PCT/GB94/00237, Apr. 8, 1994, abandoned.

[30] Foreign Application Priority Data

| Feb. 10, 1993 | [GB] | United Kingdom | 9302636 |
| Dec. 16, 1993 | [GB] | United Kingdom | 9325712 |

[51] Int. Cl.[6] .................................................. A61K 31/70
[52] U.S. Cl. ........................................... 514/47; 536/26.26
[58] Field of Search ............................. 514/47; 536/26.26

[56] References Cited

U.S. PATENT DOCUMENTS

| 5,049,550 | 9/1991 | Zamecnik | 514/47 |
| 5,721,219 | 2/1998 | Ingall et al. | 514/47 |

FOREIGN PATENT DOCUMENTS

| 9107236 | 4/1991 | United Kingdom . |
| 9011080 | 4/1990 | WIPO . |
| 9123671 | 11/1991 | WIPO . |
| 9917488 | 10/1992 | WIPO . |

OTHER PUBLICATIONS

Cusack et al.(I), "Pharmacological Effects of Isopolar Phosphonate Analogues of ATP on $P_2$–Purinoceptors in Guinea–Pig Taenia Coli and Urinary Bladder," Br. J. Pharmac., 90(4), 791–795 (1987); Chem. Abstr., 107(1), p. 18, Abstr. No. 258t (Jul. 6, 1987).

Tseng et al., "Purinergic Receptors in the Brainstem Mediate Hypotension and Bradycardia," Hypertension, 11(2), 191–197 (1988); Chem. Abstr., 108(15), p. 124, Abstr. No. 125109x (Apr. 11, 1988).

McGuire et al., "Specificity of Adenine Nucleotide Receptor Sites: Inhibition of the Guinea Pig Taenia Coli by Adenine Nucleotide Analogs," in Physiological and Regulatory Functions of Adenosine and Adenine Nucleotides, Baer and Drummond eds., Raven Press, New York, 1979, pp. 33–43; Chem. Abstr., 92(15), p. 135, Abstr. No. 122601t (Apr. 14, 1980).

Rabinkov et al., "Interaction of ATP with Acetyl–CoA Carboxylase from Rat Liver. The Role of the Polyphosphate Chain. Affinity Labeling with Alkylating Amides of ATP and ADP," Biochemie, 72(10), 719–724 (Oct. 1990).

Gough et al.(I), "Three New Adenosine Triphosphate Analogs. Synthesis and Effects on Isolated Gut," J. Medicinal Chem., 16(10), 1188–1190 (Oct. 1973).

Cusack et al. (II), "Design, Synthesis and Pharmacology of ATP Analogues Selective for Subtypes of $P_2$–Purinoceptors," Nucleosides and Nucleotides, 10(5), 1019–1028 (1991).

Blackburn et al.(I), "Synthesis, Physical, Chemical, and Enzyme Studies on Bis–2,6–Diaminopurine β–D–Ribofuranoside $P^1,P^4$–Tetraphosphate," Nucleosides and Nucleotides, 10(1–3), 549–551 (1991).

Gough et al. (II), "Analogues of Adenosine 5'–Diphosphate—New Platelet Aggregators. Influence of Purine Ring and Phosphate Chain Substitutions on the Platelet Aggregating Potency of Adenosine 5'–Diphosphate," Molecular Pharmacology, 8, 170–177 (1972).

Stone et al., "Absence of $P^2$–Purinoceptors in Hippocampal Pathways," Br. J. Pharmac., 97, 631–635 (1989).

Tatham et al., "Characterization of the $ATP^4$–Receptor that Mediates Permeabilisation of Rat Mast Cells," Eur. J. Pharmac., 147(1), 13–21 (1988).

(List continued on next page.)

Primary Examiner—Marian C. Knode
Assistant Examiner—Eric Crane
Attorney, Agent, or Firm—Nixon & Vanderhye

[57] ABSTRACT

There are disclosed compounds of formula I,

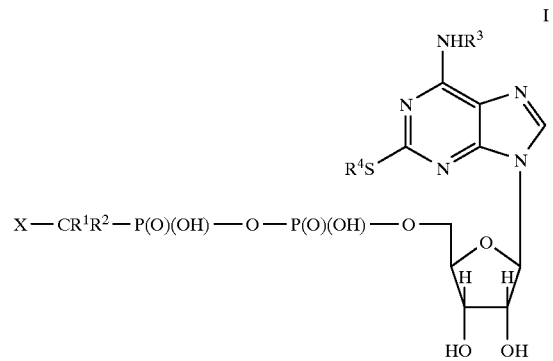

wherein $R^1$ and $R^2$ independently represent hydrogen or halogen, $R^3$ and $R^4$ independently represent phenyl, or alkyl $C_{1-6}$ optionally substituted by one or more substituents selected from $OR^5$, alkylthio $C_{1-6}$, $NR^6R^7$, phenyl, $COOR^8$ and halogen, $R^5$, $R^6$, $R^7$ and $R^8$ independently represent hydrogen or alkyl $C_{1-6}$, and X represents an acidic moiety, and pharmaceutically acceptable salts thereof. Processes for their production and pharmaceutical compositions and methods of treatment involving their use are also described.

7 Claims, No Drawings

OTHER PUBLICATIONS

Leff et al., "Quantitative Analysis of the Agonist and Antagonist Actions of Some ATP Analogues at $P_{2x}$–Purinoceptors in the Rabitt Ear Artery," *Br. J. Pharmac.*, 108(2), 490–496 (1993).

Blackburn et al.(II), "Synthesis and Resistance to Enzymatic Hydrolysis of Stereochemically–Defined Phosphonate and Thiophosphate Analogues of $P^1,P^4$–Bis(5'–Adenosyl) Tetraphosphate," *Nucleic Acids Res.*, 15(17), 6991–7004 (1987).

Tarussova et al., "The Synthesis of $P^1,P^3$–Bis(5'–Adenosyl) Triphosphate, $P^1,P^4$–Bis(5'–Adenosyl Tetraphosphate and Its Phosphonate Analogues with the Use of Carbonyl Derivatives of Nitrogen–Containing Heterocycles," *Bioorganich. Khimya.*, 12(3), 404–407 (1986); see Abstract in English at p. 407.

Guranowski et al., "Phosphonate Analogues of Diadenosine 5', 5'''–$P^1,P^4$–Tatraphosphate as Substrates or Inhibitors of Procaryotic and Eucaryotic Enzymes Degrading Dinucleoside Tetraphosphates," *Biochemistry*, 26, 3425–3429 (1987).

Kozarich et al., "Ribonucleoside Phosphate via Phosphoramidazolidate Intermediates. Synthesis of Pseudoadenosine 5'–Triphosphate," *Biochemistry*, 12(22), 4458–4463 (1973).

Blackburn et al. (III), "The Synthesis and Metal Binding Characteristics of Novel, Isopolar Phosphonate Analogues and Nucleotides," *J. Chem. Soc., Perk. Trans. I*, 1984, 1119–1125.

Cusack et al.(III), "Characterization of ADP Receptors," *Br. J. Pharmacol.*, 87, 84 (1986).

Lüthje et al. (I), "Diadenosine Triphosphate ($Ap_3A$) Mediates Human Platelet Aggregation by Liberation of ADP," *Biochem. Biophys. Res. Comm.*, 118(3), 704–709 (1984).

Lüthje et al (II), "Catabolism of $Ap_3A$ and $Ap_4A$ in Human Plasma," *Eur. J. Biochem.*, 149, 119–127 (1985).

Harrison et al., "Inhibition of Platelet Aggregation and the Platelet Release Reaction by α, ω Diadenosine Polyphosphates," *FEBS Letters*, 54(1), 57–60 (1975).

Nakajima et al., "Prosthetic Materials Coated with Antithrombogenic Diadenosine Tetraphosphate," *Chem. Abst.*, 110(6), p. 392, Abstr. No. 44985u (1989).

Chao et al., "Inhibition of Platelet Aggregation by $Ap_4A$," *Hoppe–Seyler's Z. Physiol. Chem.*, 365, 610 (1984).

Floodgaard et al., "$Ap_4A$ Determination as a Possible Tool for the Diagnosis of Chediak–Higashi Disease and Other Platelet Anamalies," *Hoppe–Seyler's Z. Physiol. Chem.*, 365, 610–611 (1984).

Louie et al., "Diadenosine 5',5'''–$p^1,p^4$–Tetraphosphate, A Potential Antithrombotic Agent," *Thrombosis Research*, 49, 557–565 (1988).

Hourani et al., "2–MeS–AMP–PCP and Human Platelets: Implications for the Role of Adenylate Cyclase in ADP–Induced Aggregation?" *Br. J. Pharmacology*, 87, 84P (1986).

Khorana, Chapter 2 ("Synthesis of Monoesters of Phosphoric Acid") and Chapter 4 ("Nucleoside Polyphosphates, Nucleotide Coenzymes, and Related Compounds of Biological Interest: Their Structure and Synthesis") in *Some Recent Developments in the Chemistry of Phosphate Esters of Biological Interest*, John Wiley & Sons, Inc., New York, NY, 1961, pp. 13–43 and 69–92, respectively.

N-ALKYL-2-SUBSTITUTED ATP ANALOGUES FOR TREATMENT OF EMBOLIC DISEASE CONDITIONS

This is a divisional of application Ser. No. 08/512,979, filed Aug. 9, 1995, now U.S. Pat. No. 5,721,219, which is a continuation of PCT/GB94/00237, filed Apr. 8, 1994, now abandoned.

This invention relates to pharmaceutically useful novel compounds, processes for their production, pharmaceutical compositions containing them and methods of treatment involving their use.

Adenosine triphosphate (ATP) has potent pharmacological effects on a variety of tissues. The activity of ATP and the other extracellular adenine nucleotides, adenosine diphosphate (ADP) and adenosine monophosphate (AMP), are mediated by $P_2$-purinoceptors. However, the potency of ATP in some tissues, e.g. the bladder, may be reduced due to rapid dephosphorylation, to AMP and adenosine, by ectonucleotidases present in these tissues.

In recent studies ATP analogues which are resistant to dephosphorylation have been used as biological probes to investigate the $P_2$-purinoceptors present in a variety of tissues:

Cusack et al, *Br. J. Pharmacol.*, 1987, 90, 791–795, describe the activity of 2-methylthio-5'-adenylic acid, monoanhydride with methylenebisphosphonic acid, 2-methylthio-5'-adenylic acid, monoanhydride with dichloromethylenebisphosphonic acid and 2-methylthio-5'-adenylic acid, monoanhydride with difluoromethylenebisphosphonic acid on the guinea pig taenia coli and urinary bladder. Stone and Cusack, *Br. J. Pharmacol.*, 1989, 97, 631–635, describe the use of inter alia 2-methylthio-5'-adenylic acid, monoanhydride with difluoromethylenebisphosphonic acid in an investigation of $P_2$-purinoceptors in the rat hippocampus. Maguire and Satchell in "Physiological and Regulatory Functions of Adenosine and Adenine Nucleotides", Ed. H. P. Baer and G. I. Drummond, Raven Press, New York, 1979, p.33–43, disclose the inhibition of guinea pig tacnia coli by the compound 2-chloro-5'-adenylic acid, monoanhydride with methylenebisphosphonic acid.

Cusack and Hourani, *Nucleosides & Nucleorides,* 1991, 10(5), 1019–1028, have also reported that 2-methylthio-5'-adenylic acid, monoanhydride with methylenebisphosphonic acid inhibits ADP-α-S induced platelet aggregation.

International Patent Application WO 92/17488 (Fisons plc) discloses a number of 2-substituted ATP analogues and their activity as inhibitors of platelet aggregation.

We have now found a group of novel N-alkyl-2-substituted ATP analogues which exhibit pharmacological activity.

According to a first aspect of the present invention, there is provided a compound of formula I,

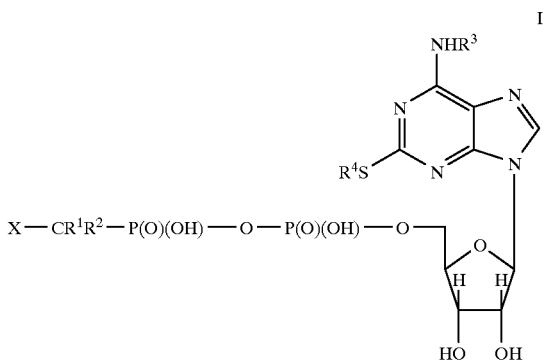

wherein $R^1$ and $R^2$ independently represent hydrogen or halogen, $R^3$ and $R^4$ independently represent phenyl, or alkyl $C_{1-6}$ optionally substituted by one or more substituents selected from $OR^5$, alkylthio $C_{1-6}$, $NR^6R^7$, phenyl, $COOR^8$ and halogen, $R^5$, $R^6$, $R^7$ and $R^8$ independently represent hydrogen or alkyl $C_{1-6}$, and X represents an acidic moiety, and pharmaceutically acceptable salts thereof.

Compounds of formula I may exist in tautomeric, enantiomeric and diastereomeric forms, all of which are included within the scope of the invention.

According to the invention there is further provided a process for the preparation of compounds of formula I, and salts thereof, which comprises:

a) reacting a compound of formula II, or a salt thereof,

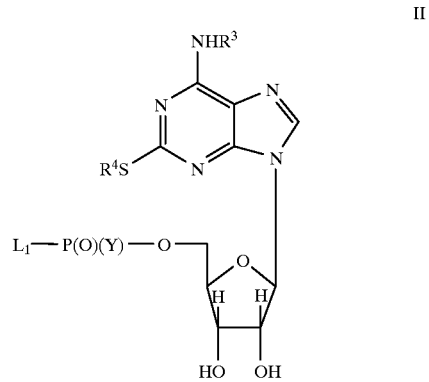

wherein $R^3$ and $R^4$ are as defined above, $L_1$ represents a leaving group, and Y represents (i) OH, or (ii) a leaving group $L_2$ with a compound of formula III, or a salt thereof,

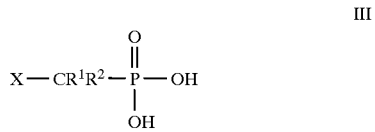

wherein $R^1$, $R^2$ and X are as defined above; followed, in the case where Y represents $L_2$ by hydrolysis, b) removal of a protecting group from a corresponding protected compound of formula I in which one or more of the functional groups is protected, and where desired or necessary converting the resultant compound of formula I, or another salt thereof, to a pharmaceutically acceptable salt thereof or vice versa.

In process a)(i), when Y represents OH, leaving groups which $L_1$ may represent include amines, for example, dialkylamines, or saturated or unsaturated cyclicamines; particular leaving groups which may be mentioned include morpholinyl, imidazolyl and triazolyl. The reaction is preferably carried out in a solvent, preferably a dipolar aprotic solvent, for example, pyridine, dimethylformamide, acetonitrile, hexamethylphosphorictriamide, N,N'-dimethylpropyleneurea or 1-methyl-2-pyrrolidinone. The reaction may be carried out at a temperature of from –20 to 100° C., e.g. from 10 to 30° C.

Compounds of formula II in which Y represent OH are either known or may be prepared using methods known to those skilled in the art, for example by techniques analogous to those described in International Patent Application WO 92/17488 (Fisons plc). For example, compounds of formula II in which $L_1$ represents morpholinyl may be prepared from the corresponding 5'-monophosphates by treatment with morpholine in the presence of a condensing agent such as dicylohexylcarbodiimide, preferably in the presence of a protic solvent or mixture of solvents such as t-butanol and water.

In process a)(ii), when Y represents $L_2$, leaving groups that $L_1$ and $L_2$ may represent include halogen e.g. chlorine. $L_1$ and $L_2$ may be different but are preferably the same. Compounds of formula II in which Y represents $L_2$ may be prepared from the corresponding nucleoside by reaction with a phosphorylating agent bearing three leaving groups, i.e. $POL_1L_2L_3$; particular phosphorylating agents which may be mentioned include $POCl_3$. The resulting compound of formula II need not be isolated but may be reacted in situ with the compound of formula III, followed by hydrolysis, e.g. base catalysed hydrolysis using $Na_2CO_3$.

The nucleosides and nucleoside 5'-monophosphates used in the preparation of the compounds of formula II are either known or may be prepared from known compounds using known techniques. See, for example, "Chemistry of Nucleosides and Nucleotides" Vol. 2, Ed. Leroy B. Townsend, Plenum Press 1991.

The compounds of formula III are either known or may be prepared from known compounds using known techniques as described, for example, in International Patent Application WO 92/17488 (Fisons plc).

In the above process it may be necessary for any functional groups, e.g. hydroxy or amino groups, present in the starting materials to be protected, thus process b) may involve the removal of one or more protecting groups.

Suitable protecting groups and methods for their removal are, for example, those described in "Protective Groups in Organic Synthesis" by T. Greene and P. G. M. Wutts, John Wiley and Sons Inc., 1991. Hydroxy groups may, for example, be protected by arylmethyl groups such as phenylmethyl, diphenylmethyl or triphenylmethyl; acyl groups such as acetyl, trichloroacetyl or trifluoroacetyl; or as tetrahydropyranyl derivatives. Suitable amino protecting groups include arylmethyl groups such as benzyl, (R,S)-α-phenylethyl, diphenylmethyl or triphenylmethyl, and acyl groups such as acetyl, trichloroacetyl or trifluoroacetyl. Conventional methods of deprotection may be used including hydrogenolysis, acid or base hydrolysis, or photolysis. Arylmethyl groups may, for example, be removed by hydrogenolysis in the presence of a metal catalyst e.g. palladium on charcoal. Tetrahydropyranyl groups may be cleaved by hydrolysis under acidic conditions. Acyl groups may be removed by hydrolysis with a base such as sodium hydroxide or potassium carbonate, or a group such as trichoroacetyl may be removed by reduction with, for example, zinc and acetic acid.

The compounds of formula I, and salts thereof, may be isolated from their reaction mixtures using conventional techniques.

The teachings of the documents mentioned above are herein incorporated by reference.

Salts of the compounds of formula I may be formed by reacting the free acid, or a salt thereof, or the free base, or a salt or derivative thereof, with one or more equivalents of the appropriate base or acid. The reaction may be carried out in a solvent or medium in which the salt is insoluble or in a solvent in which the salt is soluble, e.g. ethanol, tetrahydrofuran or diethyl ether, which may be removed in vacuo or by freeze drying. The reaction may also be a metatherical process or it may be carried out on an ion exchange resin.

Pharmaceutically acceptable salts of the compounds of formula I include alkali metal salts, e.g. sodium and potassium salts; alkaline earth metal salts, e.g. calcium and magnesium salts; salts of the Group III elements, e.g. aluminium salts; and ammonium salts. Salts with suitable organic bases, for example, salts with hydroxylamine; lower alkylamines, e.g. methylamine or ethylamine; with substituted lower alkylamines, e.g. hydroxy substituted alkylamines; or with monocyclic nitrogen heterocyclic compounds, e.g. piperidine or morpholine; and salts with amino acids, e.g. with arginine, lysine etc, or an N-alkyl derivative thereof; or with an aminosugar, e.g. N-methyl-D-glucamine or glucosamine. The non-toxic physiologically acceptable salts are preferred, although other salts are also useful, e.g. in isolating or purifying the product.

The compounds of formula I may exhibit tautomerism, e.g. imine-enamine tautomerism at the 6-position of adenine. The compounds also contain one or more asymmetric carbon atoms and therefore exhibit optical and/or diastereoisomerism. Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation.

Alkyl groups which $R^3$ and $R^4$ may represent include straight, branched or cyclic, saturated or unsaturated alkyl groups.

Halogens which $R^1$ and $R^2$ may represent include F, Cl, Br and I.

We prefer compounds in which $R^1$ and $R^2$ are the same. We particularly prefer compounds in which $R^1$ and $R^2$ represent Cl.

We prefer compounds in which $R^3$ and $R^4$ represent alkyl $C_{1-6}$ optionally substituted by one or more substituents selected from $OR^5$, alkylthio $C_{1-6}$, $NR^6R^7$, phenyl, $COOR^8$ and halogen.

Halogens with which $R^3$ and $R^4$ may be substituted include Cl, Br and I, and especially F.

We particularly prefer compounds in which $R^3$ represents alkyl $C_{1-6}$ optionally substituted by alkylthio $C_{1-6}$. Particular alkyl groups that $R^3$ may represent include propyl and butyl, and especially ethyl. Particular substituted alkyl groups that $R^3$ may represent include 2-(methylthio)ethyl.

We particularly prefer compounds in which $R^4$ represents alkyl $C_{1-6}$ optionally substituted by one or more, e.g. three, halogen atoms. Particular groups that $R^4$ may represent include propyl and 3,3,3-trifluoropropyl.

Acidic moieties which X may represent include Bronsted-Lowry acids, i.e. moieties which act as proton donors. The acidic moiety may be mono- or poly-acidic. Specific acidic moieties which may be mentioned include —P(O)(OH)$_2$, —SO$_3$H and —CO$_2$H.

We prefer compounds of formula I in which Z represents —P(O)(OH)$_2$.

The compounds of formula I are useful because they exhibit pharmacological activity in mammals. In particular, they show activity in the prevention of platelet aggregation.

The potency of the compounds of formula I as inhibitors of platelet aggregation may be determined from their ability to act as $P_{2T}$ receptor antagonists, see Example X.

The compounds may be used in any condition where platelet aggregation is involved. The compounds may thus act as anti-thrombotic agents and are indicated in treatment of prophylaxis of unstable angina, thromboembolic stroke and peripheral vascular disease. They are also indicated in the treatment or prophylaxis of the sequelae of thrombotic complications from angioplasty, thrombolysis, endarterctomy, coronary and vascular graft surgery, renal dialysis and cardio-pulmonary bypass.

Further indications include the treatment or prophylaxis of disseminated intravascular coagulation, deep vein thrombosis, pre-eclampsia/eclampsia tissue salvage following surgical or accidental trauma, vaculitis, arteritis, thrombocythaemia, ischemia and migraine.

According to a further aspect of the invention, we therefore provide the compounds of formula I, as defined above, as pharmaceuticals.

Further, we provide the use of a compound of formula I, or a pharmaceutically acceptable salt thereof, in the manufacture of a pharmaceutical composition for the treatment of a condition where platelet aggregation is involved.

The dosage to be administered will vary widely, depending on, amongst other factors, the particular compound of formula I employed, the mode of administration, the condition to be treated and its severity. However, in general, a total daily dose of from 0.1 mg to 1000 mg may be suitable for man, which may be administered in divided doses e.g. up to 6 times per day. If the compound is to be administered by infusion then typical a typical dosage rate for man is e.g. 0.5 $\mu g \cdot kg^{-1} \cdot min^{-1}$.

The compounds will generally be administered in the form of a pharmaceutical composition.

Thus, according to a further aspect of the invention there is provided a pharmaceutical composition including preferably less than 80% w/w, more preferably less than 50% w/w, e.g. 0.1 to 20%, of a compound of formula I, or a pharmaceutically acceptable salt thereof, as defined above, in admixture with a pharmaceutically acceptable diluent or carrier.

We also provide a process for the production of such a pharmaceutical composition which comprises mixing the ingredients.

Examples of pharmaceutical formulations which may be used, and suitable diluents or carriers, are as follows:

for intravenous injection or infusion—purified water or saline solution;

for inhalation compositions—coarse lactose;

for tablets, capsules and dragees—microcrystalline cellulose, calcium phosphate, diatomaceous earth, a sugar such as lactose, dextrose or mannitol, talc, stearic acid, starch, sodium bicarbonate and/or gelatin;

for suppositories—natural or hardened oils or waxes.

When the compound is to be used in aqueous solution, e.g. for infusion, it may be necessary to incorporate other excipients. In particular there may be mentioned chelating or sequestering agents, antioxidants, tonicity adjusting agents, pH-modifying agents and buffering agents.

Solutions containing a compound of formula I may, if desired, be evaporated, e.g. by freeze drying or spray drying, to give a solid composition, which may be reconstituted prior to use.

When not in solution, the compound of formula I preferably is in a form having a mass median diameter of from 0.01 to 10 $\mu$m. The compositions may also contain suitable preserving, stabilising and wetting agents, solubilisers, e.g. a water-soluble cellulose polymer such as hydroxypropyl methylcellulose, or a water-soluble glycol such as propylene glycol, sweetening and colouring agents and flavourings. Where appropriate, the compositions may be formulated in sustained release form.

According to a further aspect of the invention, we provide a method of treating a condition where platelet aggregation is involved which comprises administering a therapeutically effective amount of a compound of formula I, as defined above, to a patient suffering from such a condition.

The compounds of the invention are advantageous in that they may produce fewer side effects e.g. have a reduced capacity to produce hypothermia as determined by the procedure of Example Y, may have advantageous duration, may be less toxic, more efficacious, more potent, more stable, more easily absorbed, more readily cleared from the body, exhibit a broader range of activity, or have other useful pharmacological properties, when compared with compounds known from the prior art.

The invention is illustrated, but in no way limited, by the following Examples, in which temperatures are given in degrees Celsius. Examples are named using Chemical Abstracts nomenclature.

EXAMPLE 1

N-Ethyl-2-(propylthio)-5'-adenylic Acid, Monoanhydride With Dichloromethylenebisphosphonic Acid, Tetrasodium Salt a) N-Ethyl-2-(propylthio)adenosine 9-(2,3,5-Tri-O-acetyl-β-D-ribofuranosyl)-6-chloro-2-(propylthio)purine (1.3 g) and ethylamine (1.6 ml) in dioxane (30 ml) and water (30 ml) were heated in a sealed autoclave at 110° for 20 hours. On cooling to room temperature, evaporation gave a residue which was recrystallised from ethyl acetate. Further purification by chromatography (SiO$_2$, methanol:ethyl acetate, 1:15 as eluant) gave the sub-title compound (0.46 g).

MS (FAB): 370 (M+H, 100%), 238 (30%).

b) N-Ethyl-2-(propylthio)-5'-adenylic Acid, Monoammonium Salt

Phosphorus oxychloride (0.66 g) was added to a stirred solution of the product of step a) (0.4 g) in triethyl phosphate (12 ml) at 0°. After 4½ hours the reaction mixture was poured onto ice/water (100 g) containing sodium hydrogen carbonate (1.45 g). After 45 min the solution was washed with ether (2×100 ml) and applied to a column of Dowex 50W×8 (H⁺ form). The column was washed with water until the eluate was at pH 6, then eluted with 2M ammonium hydroxide. Lyophilisation gave the sub-title compound (0.32 g).

$^{31}$P NMR δ (D$_2$O): 2.03 (s).

c) N-Ethyl-2-(propylthio)-5'-adenylic Acid, Monoanhydride With Dichloromethylenebisphosphonic Acid, Tetrasodium Salt The product of step b) (0.38 g) and tributylamine (0.15 g) were combined in a small volume of pyridine and the solution evaporated to dryness. Azeotropic drying with pyridine (3×15 ml) followed by anhydrous N,N-dimethylformamide (DMF) (2×15 ml) left a residue which was taken into anhydrous DMF (10 ml). Carbonyldiimidazole (0.66 g) was added and the reaction left at room temperature for 4 hours before adding methanol (0.209 g). After 30 min. dichloromethylenebisphosphonic acid, mono (tributylammonium) salt (2.09 g) in anhydrous DMF (30 ml) was added and the mixture stirred at room temperature for 18 hours. Filtration and evaporation afforded a residue which was purified by chromatography (DEAE-Sephadex, triethylammonium bicarbonate 0M to 0.6M as eluant). Lyophilisation gave the triethylammonium salt which was converted to the sodium form by dissolution in methanol (2 ml) and addition of sodium iodide solution (1M in acetone, 30 ml). The precipitate was collected by centrifugation, washing by repeated suspension in acetone (4×40 ml) and recentrifugation. Finally the solid was dissolved in water and lyophilised to give the title salt as a colourless powder (0.25 g).

$^{31}$P NMR δ (D$_2$O): 9.00 (d, J=18.6 Hz), 1.18 (dd, J=18.6 Hz, J=30.4 Hz), −9.35 (d, J=30.4 Hz).

EXAMPLE 2

N-Butyl-2-(propylthio)-5'-adenylic Acid, Monoanhydride With Dichloromethylenebisphosphonic Acid, Tetrasodium Salt a) N-Butyl-2-(propylthio)adenosine

The sub-title compound was prepared according to the method of Example 1a).

MS (FAB): 398 (M+H⁺, 100%).

b) N-Butyl-2-(propylthio)-5'-adenylic Acid, Monoanhydride With Dichloromethylenebisphosphonic Acid, Tetrasodium Salt Phosphorus oxychloride (1.39 g) was added dropwise, with cooling, to a solution of the product of step a) (1.8 g) in triethyl phosphate (50 ml). The resulting solution was stirred at room temperature for 4 hours.

Tributylamine (2.16 ml) was added to a stirred suspension of dichloromethylenebisphosphonic acid, mono (tributylammonium) salt (5.76 g) in triethyl phosphate (60 ml). After stirring at room temperature for 1 hour the resulting solution was added over 15 min to the solution described above. Upon stirring for a further 4 hours the reaction mixture was poured onto a 5% aqueous sodium bicarbonate solution (113 ml) then stirred for 18 hours. The resulting solution was washed with ether (4×50 ml) then freeze-dried. Purification (Reversed-phase C$_{18}$ silica, 4% saline followed by water as eluant) gave the title salt as a colourless solid (0.69 g).

$^{31}$P NMR δ (D$_2$O): 9.70 (d, J=18.4 Hz), 3.4 (dd, J=18.4 Hz, J=30.5 Hz), −9.19 (d, J=30.5 Hz).

EXAMPLE 3

The following compounds were prepared according to the method of Example 2.

a) N-Propyl-2-(propylthio)-5'-adenylic Acid, Monoanhydride With Dichloromethylenebisphosphonic Acid, Tetrasodium Salt i. N-Propyl-2-(propylthio)adenosine
  MS (FAB: 384 (M+H⁺, 100%).
ii. N-Propyl-2-(propylthio)-5'-adenylic Acid, Monoanhydride With Dichloromethylenebisphosphonic Acid, Tetrasodium Salt
  $^{31}$P NMR δ (D$_2$O): 8.92 (d, J=18.5 Hz), 1.07 (dd, J=18.7 Hz, J=29.0 Hz), −9.4 (d, J=29.4 Hz).

b) N-(1-Methylethyl)-2-(propylthio)-5'-adenylic Acid, Monoanhydride With Dichloromethylenebisphosphonic Acid, Diammonium Salt i. N-(1-Methylethyl)-2-(propylthio)adenosine
  MS (FAB): 384 (M+H$^{30}$, 100%), 252.
ii. N-(1-Methylethyl)-2-(propylthio)-5'-adenylic Acid, Monoanhydride With Dichloromethylenebisphosphonic Acid Diammonium Salt Further purification of the crude product by chromatography (DEAE-Sephadex, ammonium bicarbonate solution, 0M to 0.6M as eluant) gave the title salt.

$^{31}$P NMR δ (D$_2$O): 8.71 (d, J=18.6 Hz), 0.38 (dd, J=19.1 Hz, J=28.7 Hz), −9.49 (d, J=29.0 Hz).

c) N-(2-Methoxyethyl)-2-(propylthio)-5'-adenylic Acid, Monoanhydride With Dichloromethylenebisphosphonic Acid, Tetrasodium Salt i. N-(2-Methoxyethyl)-2-(propylthio)adenosine
  MS (FAB): 400 (M+H⁺, 100%), 268.
ii. N-(2-Methoxyethyl)-2-(propylthio)-5'-adenylic Acid, Monoanhydride With Dichloromethylenebisphosphonic Acid, Tetrasodium Salt
  $^{31}$P NMR δ (D$_2$O): 9.05 (d, J=18.7 Hz), 1.44 (dd, J=18.8 Hz, J=29.3 Hz). −9.40 (d, J=29.5 Hz).

d) N-Cyclopentyl-2(propylthio)-5'-adenylic Acid, Monoanhydride With Dichloromethylenebisphosphonic Acid, Tetrasodium Salt i. N-Cyclopentyl-2-(propylthio)adenosine
  MS (FAB): 410 (M+H⁺), 278 (100%).
ii. N-Cyclopentyl-2-(propylthio)-5'-adenylic Acid, Monoanhydride With Dichloromethylenebisphosphonic Acid, Tetrasodium Salt
  Analysis found C:24.43; H:4.43; N:7.52; S:3.76%; C$_{19}$H$_{26}$Cl$_2$N$_5$Na$_4$O$_{12}$P$_3$S.7H$_2$O requires C:24.56; H:4.30; N:7.53; S:3.44%.

e) N-Phenyl-2-(propylthio)-5'-adenylic Acid, Monoanhydride With Difluoromethylenebisphosphonic Acid, Tetrasodium Salt i. N-Phenyl-2-(propylthio)adenosine
  MS (FAB): 418 (M+H⁺, 100%), 278.

ii. N-Phenyl-2-(propylthio)-5'-adenylic Acid, Monoanhydride With Dichloromethylenebisphosphonic Acid, Tetrasodium Salt $^{31}$P NMR δ (D$_2$O): 8.98 (d, J=18.3 Hz), 2.70 (dd, J=18.3 Hz, J=30.6 Hz), −9.89 (d, J=30.6 Hz).

f) N-(2,2,2-Trifluoroethyl)-2-(propylthio)-5'-adenylic Acid, Monoanhydride With Dichloromethylenebisphosphonic Acid, Tetrasodium Salt i. N-(2,2,2-Trifluoroethyl)-2-(propylthio)adenosine
MS (FAB): 424 (M+H$^+$), 292 (100%).
ii. N-(2,2,2-Trifluoroethyl)-2-(propylthio)-5'-adenylic Acid, Monoanhydride With Dichloromethylenebisphosphonic Acid, Tetrasodium Salt
MS (FAB): 822, 820, 818 (M+H$^+$), 115 (100%).

g) N-(Methoxycarbonylmethyl)-2-(propylthio)-5'-adenylic Acid, Monoanhydride With Dichloromethylenebisphosphonic Acid, Triammonium Salt i. N-(Methoxycarbonylmethyl)-2-(propylthio)adenosine
Analysis found C:46.44; H:5.43; N:16.80; S:7.67%; C$_{16}$H$_{23}$N$_5$O$_6$S requires C:46.48; H:5.61; N:16.94; S:7.76%.
ii. N-(Methoxycarbonylmethyl)-2-(propylthio)-5'-adenylic Acid, Monoanhydride With Dichloromethylenebisphosphonic Acid, Triammonium Salt
Further purification of the crude product by chromatography (DEAE-Sephadex, ammonium bicarbonate solution, 0M to 0.6M as eluant) gave the title salt.
$^{31}$P NMR δ (D$_2$O): 9.05 (d, J=18.7 Hz), 1.44 (dd, J=18.8 Hz, J=29.3 Hz), −9.40 (d, J=29.5 Hz).

h) N-[2-(Methylthio)ethyl]-2-(propylthio)-5'-adenylic Acid, Monoanhydride With Dichloromethylenebisphosphonic Acid, Triammonium Salt i. N-[2-(Methylthio)ethyl]-2-(propylthio)adenosine
MS (FAB): 416 (M+H$^+$, 100%).
ii. N-[2-Methylthio)ethyl]-2-(propylthio)-5'-adenylic Acid, Monoanhydride With Dichloromethylenebisphosphonic Acid, Triammonium Salt
Further purification of the crude product by chromatography (DEAE-Sephadex, ammonium bicarbonate solution, 0M to 0.6M as eluant) gave the title salt.
$^{31}$P NMR δ (D$_2$O): 8.68 (d, J=18.6 Hz), 0.33 (dd, J=18.9 Hz, J=29.0 Hz), −9.53 (d, J=29.0 Hz).

i) N-[2-(N,N-Dimethylamino)ethyl]-2-(propylthio)-5'-adenylic Acid, Monoanhydride With Dichoromethylenebisphosphonic Acid, Trisodium Salt i. N-[2-(N,N-Dimethylamino)ethyl]-2-(propylthio)adenosine
MS (FAB): 413 (M+H$^+$, 100%).
ii. N-[2-(N,N-Dimethylamino)ethyl]-2-(propylthio)-5'-adenylic Acid Monoanhydride with Dichoromethylenebisphosphonic Acid, Trisodium Salt
MS (FAB): 789, 787, 785 (M+H$^+$), 93 (100%).

EXAMPLE 4

2-(Cyclohexylthio)-N-ethyl-5'-adenylic Acid, Monoanhydride With Dichloromethylenebisphosphonic Acid, Tetrasodium Salt a) 9-(2,3,5-Tri-O-acetyl-β-D-ribofuranosyl)-6-chloro-2-(cyclohexylthio)purine Dicyclohexyldisulfide (51.5 g) and isoamyl nitrite (16.96 g) were added to a solution of 2-amino-9-(2,3,5-trio-O-acetyl-β-D-ribofuranosyl)-6-chloropurine (10.0 g) in acetonitrile (200 ml). The solution was degassed with nitrogen then heated at 60° for 16 hours. The solution was concentrated and the residue purified (SiO$_2$, ethyl acetate:petroleum ether, 1:1 as eluant) to give the sub-title compound as an orange gum (3.88 g).
MS (EI): 528, 526 (M$^+$), 43 (100%).

b) 2-(Cyclohexylthio)-N-ethyl-adenosine

The sub-title compound was prepared according to the method of Example 1a) using the product of step a).
MS (FAB): 410 (M+H$^+$, 100%).

c) 2-(Cyclohexylthio)-N-ethyl-5'-adenylic Acid, Monoanhydride With Dichloromethylenebisphosphonic Acid, Tetrasodium Salt The title salt was prepared according to the method of Example 2b) using the product of step b).
$^{31}$P NMR δ (D$_2$O): 9.85 (d, J=18.5 Hz), 3.85 (dd, J=18.5 Hz, J=30.4 Hz), −9.07 (d, J=30.4 Hz).

EXAMPLE 5

N-Ethyl-2-[(3,3,3-trifluoropropyl)thio]-5'-adenylic Acid, Monoanhydride With Dichloromethylenebisphosphonic Acid, Trisodium Salt a) 2-[(3,3,3-Trifluoropropyl)thio]adenosine

A suspension of sodium hydride (60%, 1.453 g) and adenosine-2-thione monohydrate (5.35 g) in DMF (80 ml) was stirred at room temperature for 1 hour before adding 3-chloro-1,1,1-trifluoropropane (6.6 ml). After stirring for 5 days the solution was concentrated and the residue partitioned between ethyl acetate (250 ml) and water (150 ml). The organic phase was dried then concentrated. Purification (SiO$_2$, dichloromethane:methanol, 9:1 as eluant) gave the sub-title compound as a colourless solid (5.55 g).
MS (FAB): 396 (M+H$^+$, 100%).

b) N-Acetyl-2-[(3,3,3-trifluoropropyl)thio] adenosine-2',3',5'-triacetate

The product of step a) (5.28 g) and anhydrous sodium acetate (0.723 g) in acetic anhydride (42 ml) were stirred at 80° for 6½ hours. The solution was diluted with water (100 ml), stirred at room temperature for 18 hours then extracted with dichloromethane (4×200 ml). The combined organic extracts were washed with saturated sodium bicarbonate solution (200 ml) then evaporated and the residue chromatographed (SO$_2$, diethyl ether:methanol, 97:3 as eluant) to give the sub-title compound as a colourless foam (5.35 g).
MS (FAB): 564 (M+H$^+$), 139 (100%).

c) N-Acetyl-N-ethyl-2-[(3,3,3-trifluoropropyl)thio] adenosine-2',3',5'-triacetate The product of step b) (5.12 g) in DMF (100 ml) was added over 3 hours to a suspension of sodium hydride (60%, 0.443 g) in DMF (100 ml) containing ethyl iodide (2.2 ml). After stirring for 2 days the solution was evaporated and the residue taken into ethyl acetate (33 ml) then washed with water (3×100 ml). The organic phase was concentrated and the residue purified (SiO$_2$, ethyl acetate:cyclohexane, 1:1 as eluant) to give the sub-title compound as a yellow gum (4.54 g).

MS (FAB): 592 (M+H⁺), 139 (100%).

d) N-Ethyl-2-[(3,3,3-trifluoropropyl)thio]adenosine

The product of step c) (4.54 g) in sodium hydroxide solution (0.1M in methanol, 155 ml) was heated at reflux for 30 min. On cooling to room temperature, glacial acetic acid (0.89 ml) was added and the solution concentrated. Purification (SiO$_2$, dichloromethane:methanol, 95:5 as eluant) gave the sub-title compound as a colourless solid (2.73 g).

MS (FAB): 424 (M+H⁺, 100%).

e) N-Ethyl-2-[(3,3,3-trifluoropropyl)thio]-5'-adenylic Acid, Monoanhydride With Dichloromethylenebisphosphonic Acid, Trisodium Salt The title salt was prepared according to the method of Example 2b) using the product of step d).

$^{31}$P NMR δ (D$_2$O): 8.89 (d, J=18.0 Hz), 2.34 (dd, J=18.0 Hz, J=30.0 Hz), −9.90 (d, J=30.0 Hz).

EXAMPLE 6

The following compounds were prepared according to the method of Example 2:

a) N-(2,2,2-Trifluoroethyl)-2-[(3,3,3-trifluoropropyl)thio]-5'-adenylic Acid, Monoanhydride With Dichloromethylenebisphosphonic Acid, Triammonium Salt i. N-Acetyl-N-(2,2,2-trifluoroethyl)-2-[(3,3,3-trifluoropropyl)thio]adenosine-2',3',5'-triacetate
MS (FAB): 646 (M+H⁺).

ii. N-(2,2,2-Trifluoroethyl)-2-[(3,3,3-trifluoropropyl)thio]adenosine
MS (FAB): 478 (M+H⁺), 346 (100%).

iii. N-(2,2,2-Trifluoroethyl)-2-[(3,3,3-trifluoropropyl)thio]-5'-adenylic Acid, Monoanhydride with Dichloromethylenebisphosphonic Acid, Triammonium Salt
$^{31}$P NMR δ (D$_2$O): 8.82 (d, J=18.6 Hz), 0.63 (dd, J=18.9 Hz, J=28.9 Hz), −9.43 (d, J=29.0 Hz).

b) N-[2-(Methylthio)ethyl]-2-[(3,3,3-trifluoropropyl)thio]-5'-adenylic Acid, Monoanhydride With Dichloromethylenebisphosphonic Acid, Triammonium Salt i. N-Acetyl-N-[2-(Methylthio)ethyl]-2-[(3,3,3-trifluoropropyl)thio]adenosine-2',3',5'-triacetate
MS (FAB): 638 (M+H⁺), 139 (100%).

ii. N-[2-(Methylthio)ethyl]-2-[(3,3,3-trifluoropropyl)thio]adenosine
Analysis found C:40.70; H:4.82; N:14.79; S:13.60%; C$_{16}$H$_{22}$F$_3$N$_5$O$_4$S$_2$ requires C:40.90; H:4.72; N:14.92; S:13.70%.

iii. N-[2-(Methylthio)ethyl]-[(3,3,3-trifluoropropyl)thio]-5'-adenylic Acid, Monoanhydride With Dichloromethylenebisphosphonic Acid, Triammonium Salt Further purification of the crude product by chromatography (DEAE-Sephadex, ammonium bicarbonate solution, 0M to 0.6M as eluant) gave the title salt.

$^{31}$P NMR δ (D$_2$O): 8.77 (d, J=18.7 Hz), 0.38 (dd, J=18.9 Hz, J=27.4 Hz), −9.43 (d, J=28.8 Hz).

EXAMPLE 7

N-(2-Methoxyethyl)-2-[(3,3,3-trifluoropropyl)thio]-5'-adenylic Acid, Monoanhydride With Dichloromethylenebisphosphonic Acid, Tetrasodium Salt a) N-(2-Methoxyethyl)-2-[(3,3,3-trifluoropropyl)thio]adenosine A solution of the compound of Example 5b) (4.8 g), 2-bromoethyl methyl ether (1.2 ml) and potassium carbonate (1.77 g) in dry DMF (190 ml) was stirred at room temperature for 3 days. Further quantities of 2-bromoethyl methyl ether (1.2 ml) and potassium carbonate (1.77 g) were added and the mixture stirred at 40° for 24 hours. The reaction mixture was filtered and the filtrate concentrated to give an oil which was partitioned between ethyl acetate (200 ml) and water (200 ml). The organic phase was dried then concentrated. The resulting gum was dissolved in a 0.1M solution of sodium methoxide in methanol (180 ml) then heated at reflux for 45 min. After neutralising with acetic acid the solution was concentrated and the residue purified (SiO$_2$, dichloromethane:methanol, 92:8 as eluant) to give the sub-title compound as a colourless solid (3.41 g).

MS (FAB): 454 (M+H⁺, 100%).

b) N-(2-Methoxyethyl)-2-[(3,3,3-trifluoropropyl)thio]-5'-adenylic Acid, Monoanhydride With Dichloromethylenebisphosphonic Acid, Tetrasodium Salt The title salt was prepared according to the method of Example 2b) using the compound of step a).

$^{31}$P NMR δ (D$_2$O): 9.88 (d, J=19.0 Hz), 3.80 (dd, J=19.0 Hz, J=31.0 Hz), −9.12 (d, J=31.0 Hz).

EXAMPLE X

Quantification of P-$_5$ Receptor Agonist/Antagonist Activity in Washed Human Platelets Preparation Human venous blood (100 ml) was divided equally between 3 tubes, each containing 3.2% trisodium citrate (4 ml) as anti-coagulant. The tubes were centrifuged for 15 min at 240G to obtain a platelet-rich plasma (PRP) to which 300 ng·ml$^{-1}$ prostacyclin (PGI$_2$, 3 µl·ml$^{-1}$ PRP of ¹⁄₁₀ diln. in saline from stock 1 mg·ml$^{-1}$ in ethanol) was added to stabilize the platelets during the washing procedure. Red cell free PRP was obtained by centrifugation for 10 min at 125G followed fur further centrifugation for 15 min at 640G. The supernatant was discarded and the platelet pellet resuspended in modified, calcium free, Tyrode solution [(10 ml) CFT, composition: NaCl 137 mM (8 g·l$^{-1}$), NaHCO$_3$ 11.9 mM (1 g·l$^{-1}$), NaH$_2$PO$_4$ 0.38 mM (0.06 g·l$^{-1}$), KCl 2.86 mM (1 ml of 20% soln·l$^{-1}$), MgCl$_2$ 1.05 mM (1 ml of 10% soln·l$^{-1}$), dextrose 5.55 mM (1 g·l$^{-1}$)], gassed with 95%, O$_2$/5% CO$_2$ and maintained at 37°. Following addition of a further 300 ng·ml$^{-1}$ PGI$_2$, the pooled suspension was centrifuged once more for 15 min at 640G. The supernatant was discarded and the platelets resuspended initially in 10 ml CFT with further CFT added to adjust the final platelet count to 2×10$^5$ µl$^{-1}$. This final suspension was stored in a 60 ml syringe at 3° with air excluded.

To allow recovery from PGI$_2$-inhibition of normal function, platelets were used in aggregation studies no sooner than 2 hours after final resuspension. In all studies 430 µl aliquots of platelet suspension were added to siliconized aggregation cuvettes containing CaCl$_2$ solution (10 µl of 45 mM solution, final concentration 1 mM) and stirred at 900 rpm in a PAP4 aggregometer (Biodata). Human fibrinogen (Sigma, F 4883) and 8-sulphophenyltheophylline (8-SPT, to block and P$_1$ agonist activity of compounds) were added to give final concentrations of 0.2 mg/ml (10 µl of 10 mg·ml$^{-1}$ solution of clottable protein in saline) and 3×10$^{-1}$M (10 µl of 5.6 mg·ml$^{-1}$ solution in 6% glucose), respectively. Recording of aggregation was then started.

Protocol a) Selection of Submximal ADP Concentration

A concentration of ADP producing a just submaximal response was selected by constructing a concentration/response curve over the range 10–300 μM. The appropriate solution of ADP was added to the aggregation cuvette in a volume of 10 μl, 20 min after starting the aggregation trace. Aggregation responses were measured using the maximum rate of change in light transmission, an index given by the PAP4 slope-reader. The submaximal concentration of ADP selected at this stage of the protocol was used in the subsequent assessment of antagonist potency of the compounds. All measurements were made in duplicate in platelets from each donor.

b) Assessment of Agonist/Antagonist Potency 5 min after starting the aggregation trace, saline or the appropriate solution of test compound was added to an aggregation cuvette in a volume of 30 μl to give a final concentration of 0, 10, 100 or 1000 μM. Aggregation at this point was indicative of agonist activity and, if it occurred, agonist potency was estimated by comparison with control ADP responses obtained in a).

If aggregation did not occur the previously selected submaximal concentration of ADP was added in a volume of 10 μl, 15 min after the test compound. Antagonist potency was estimated as a % inhibition of the control ADP response to obtain an approximate $IC_{50}$. Compounds which completely inhibited the ADP response at the initial concentrations were retested at a lower concentration range. Compounds with an $IC_{50} < 10^{-8}$M were also retested in the absence of 8-SPT to confirm the lack of any $P_1$ agonist activity and with a 2 min rather than a 15 min incubation to check whether inhibition was time dependent.

Results

Representative data obtained for the compounds of formula I are reported as the negative logarithm of the antagonist potency ($pIC_{50}$) in Table 1.

TABLE 1

| Example No. | $pIC_{50}$ |
|---|---|
| 1 | 9.04 ± 0.15 |
| 5 | 8.68 ± 0.33 |
| 6a | 9.14 ± 0.11 |

EXAMPLE Y

Measurement of Hypothermic Activity in Conscious Mice

CR/CD-1 mice (25–45 g) were used. The mice were weighed and their initial rectal temperature measured using a thermistor probe. Each animal was placed in a restraining cone and the tail vein cannulated using a 27G hypodermic needle connected to a polythene cannula and taped in position. The animal was treated with a dose of the test compound administered as a 10 min intravenous infusion at a rate of 0.5 ml·kg$^{-1}$·min$^{-1}$. Rectal temperature was measured ½, 1, 1½, 2, 3, 4, 6 and 24 hours after termination of the infusion.

The mean maximum reduction in rectal temperature was plotted against dose for the compound and the dose required to lower temperature by 5° was determined.

We claim:

1. A method for the treatment or prophylaxis of unstable angina in a patient in need of such treatment, comprising the step of administering to said patient a therapeutically effective amount of a compound of formula I:

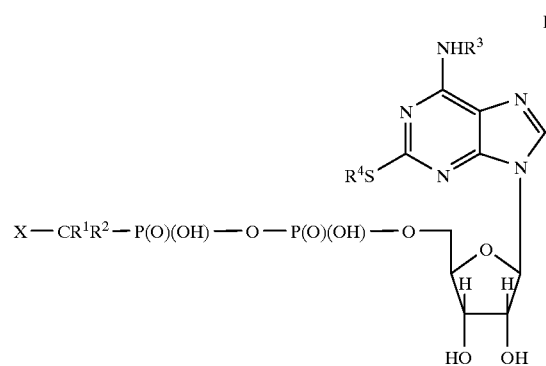

wherein $R^1$ and $R^2$ independently represent hydrogen or halogen, $R^3$ and $R^4$ independently represent phenyl or alkyl $C_{1-4}$ optionally substituted by one or more substituents $OR^5$, alkylthio $C_{1-6}$, $NR^6R^7$, phenyl, $COOR^8$ and halogen, $R^5$, $R^6$, $R^7$ and $R^8$ independently represent hydrogen or alkyl $C_{1-6}$, and X represents an acidic moiety, or a pharmaceutically acceptable salt thereof.

2. A method for the treatment or prophylaxis of peripheral vascular disease in a patient in need thereof comprising the step of administering an effective amount of a compound as defined in claim 1.

3. A method for the treatment or prophylaxis of thrombotic complications from angioplasty in a patient in need thereof comprising the step of administering an effective amount of a compound as defined in claim 1.

4. A method for the treatment or prophylaxis of the sequelae of thrombotic complications from thrombolysis in a patient in need thereof comprising the step of administering an effective amount of a compound as defined in claim 1.

5. A method for the treatment or prophylaxis of the sequelae of thrombotic complications from endarterectomy, coronary and vascular graft surgery, renal dialysis and cardiopulmonary bypass in a patient in need thereof.

6. A method for the treatment or prophylaxis of disseminated intravascular coagulation, deep vain thrombosis, preeclampsia/eclampsia, tissue salvage following surgical or accidental trauma, vasculitis, arteritis, thrombocythemia and ischaemia in a patient in need thereof.

7. A method of treatment of thromboembolic stroke in a patient in need thereof comprising the step of administering an effective amount of a compound as defined in claim 1.

* * * * *